(12) United States Patent
Walton, III

(10) Patent No.: US 9,330,235 B2
(45) Date of Patent: *May 3, 2016

(54) SYSTEM AND METHOD FOR PROVIDING ACCESS TO ELECTRONICALLY STORED MEDICAL INFORMATION

(71) Applicant: James F. Walton, III, Tallahassee, FL (US)

(72) Inventor: James F. Walton, III, Tallahassee, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 14/742,205

(22) Filed: Jun. 17, 2015

(65) Prior Publication Data

US 2016/0042126 A1 Feb. 11, 2016

Related U.S. Application Data

(63) Continuation-in-part of application No. 14/454,799, filed on Aug. 8, 2014, now Pat. No. 9,111,167.

(51) Int. Cl.
*G06K 19/00* (2006.01)
*G06F 19/00* (2011.01)

(52) U.S. Cl.
CPC .................................. *G06F 19/322* (2013.01)

(58) Field of Classification Search
USPC .......................................................... 235/487
See application file for complete search history.

(56) References Cited

U.S. PATENT DOCUMENTS

| | | | |
|---|---|---|---|
| 5,658,016 A | 8/1997 | Goeken | |
| D426,833 S | 6/2000 | Vanelli | |
| 6,513,720 B1 | 2/2003 | Armstrong | |
| 6,747,561 B1 | 6/2004 | Reeves | |
| 6,751,805 B1 | 6/2004 | Austion | |
| 6,845,063 B2 | 1/2005 | Mitchell | |
| 7,827,043 B2 | 11/2010 | Tahan | |
| 8,602,311 B2 | 12/2013 | Walton, III | 235/487 |
| 8,960,555 B1 * | 2/2015 | Walton, III | 235/487 |
| 2002/0120470 A1 | 8/2002 | Trice, Sr. | |
| 2003/0058110 A1 | 3/2003 | Rich | |
| 2003/0101077 A1 | 5/2003 | Whol | |
| 2003/0150143 A1 | 8/2003 | Hazard | |
| 2005/0194270 A1 | 9/2005 | Gombar | |
| 2006/0010012 A1 | 1/2006 | Franzblau et al. | |
| 2006/0015368 A1 | 1/2006 | Hockey | |
| 2006/0085226 A1 | 4/2006 | Kamber | |
| 2006/0142057 A1 | 6/2006 | Schuler et al. | |
| 2007/0158411 A1 | 7/2007 | Krieg, Jr. | |
| 2007/0265884 A1 | 11/2007 | Lubell et al. | |
| 2008/0126729 A1 | 5/2008 | Cai et al. | |
| 2008/0319798 A1 | 12/2008 | Kelley | |
| 2009/0076849 A1 | 3/2009 | Diller | |
| 2009/0101721 A1 | 4/2009 | Hawthorne et al. | |
| 2009/0295569 A1 | 12/2009 | Corwin et al. | |
| 2010/0115609 A1 | 5/2010 | Spence | |

* cited by examiner

*Primary Examiner* — Christle I Marshall
(74) *Attorney, Agent, or Firm* — Livingston Loeffler, P.A.; Edward M. Livingston, Esq.; Bryan L. Loeffler, Esq.

(57) ABSTRACT

A method and system for storing medical information of an individual with a service provider and providing access to that medical information to medical providers remotely. An individual's medical information may be accessed by medical providers after being authenticated by the service provider and used to pre-register or register the individual so the individual receives faster medical treatment. Access to the medical information is monitored to prevent unauthorized access and to store time and location when medical information is accessed by a medical provider. The medical information may be accessed by a mobile software application that allows the medical provider to scan a machine-readable medium linked to the individual's medical information stored by the service provider.

13 Claims, 5 Drawing Sheets

SYSTEM AND METHOD FOR PROVIDING ACCESS TO ELECTRONICALLY STORED MEDICAL INFORMATION

CROSS-REFERENCE TO RELATED APPLICATIONS

This application is a continuation-in-part of U.S. patent application Ser. No. 14/454,799 filed on Aug. 8, 2014 which is currently pending. The patent application identified above is incorporated herein by reference in its entirety to provide continuity of disclosure.

FIELD OF THE INVENTION

This invention relates to providing personal medical information to medical service providers through the use of machine-readable mediums, electronic devices and the Internet.

BACKGROUND OF THE INVENTION

During a medical emergency and/or when visiting a medical service provider for medical treatment it is important that medical providers be aware of a patient's medical history including allergies to drugs, current medications and medical conditions. It also becomes necessary to have the patient's emergency contact information and physician contact information. Conventional methods of providing such information include the patient writing out or orally providing his or her medical history and/or the medical service provider obtaining the records from the patient's past medical service provider's and physicians.

A problem arises with maintaining the security and privacy of sensitive medical information stored remotely and/or on electronic mediums. It is important to only allow access to such sensitive information to medical service providers who have been confirmed as medical providers and, thus, authorized to access an individual's medical records.

Therefore, a need exists for a system and method of providing access to electronically stored medical information that allows an authenticated medical providers to access an individual's medical information remotely and securely via an electronic device to pre-register the individual, thereby speeding up the process of the individual receiving required medical treatment.

SUMMARY OF THE INVENTION

The primary object of the present invention is to provide a system and method of providing access to electronically stored medical information that allows a user to easily store personal and medical information in a central database.

An additional object of the present invention is to provide a system and method of providing access to electronically stored medical information that provides a medical provider remote access to an individual's medical information.

An additional object of the present invention is a system and method of providing access to electronically stored medical information that allows an authenticated medical service providers to access an individual's medical information remotely and securely via an electronic device to pre-register the individual, thereby speeding up the process of the individual receiving required medical treatment.

The present invention fulfills the above and other objects by providing a system and method of providing access to electronically stored medical information, such as blood type, allergies, medical conditions, present medications, age, doctor information and emergency contact information. The medical information may be accessed directly from a machine-readable medium and/or from a remote database over the Internet wherein the medical information stored in the remote database is linked to a specific machine-readable medium and/or identification number, such as a driver's license number. This is accomplished by using a one-dimensional, two dimensional or three dimensional barcode, such as a Quick Response Code ("QR code") or other matrix barcode that is capable of storing text and/or URL information that may be opened by an electronic device or other imaging device, such as a smart phone. The barcode may be printed directly on an identification card or on a bracelet, key chain, identification card, driver's license, insurance card and/or on an adhesive-backed material and then adhered to an existing card, such as a driver's license or other identification card. Alternatively, the barcode or other machine-readable medium may be printed on a sleeve into which an identification card, such as a driver's license, is placed.

An additional advantage of the method and system of the present invention is an added layer of security for allowing access to stored medical records and information by requiring medical providers to register with the service provider and be pre-authorized by having their credentials authenticated. After the medical providers have been confirmed and pre-authorized they are allowed to use a downloadable software application from the service provider to access medical records for specific individuals. The medical providers must enter a security code or perform some other security recognition function, such as biometric recognition prior to accessing medical records. This ensures that only preauthorized medical providers are able to access an individual's medical information. This also allows the service provider to track who is accessing an individual's medical information, when the information is accessed and the geographic location of the request.

The software will be used in retrieving medical emergency information for anyone involved in an emergency situation. The software will be available preferably as a free download, and can be used by medical providers as well as the individual owner of a medical information account or his or her appointed representatives. Medical providers will be verified by a registration process with the service provider that requires them to provide their license number and/or other relevant identifying data. Once verified, the medical providers will be able to access an individual's emergency medical information. At the time of accessing the central database to obtain the individual's medical records, the medical providers can access electronic emergency medical records by: (1) Scanning 1-dimensional, 2-dimensional or 3-dimensional barcodes commonly used on driver's licenses, social services cards, national identification cards, and patient care provider cards; and/or (2) manually inputting identifying information into an electronic device, such as a driver's license number, social services card number, national identification card number, or other patient care provider number. The identifying information may be input into the electronic device using a keyboard, voice recognition, a blue-tooth device, touch screen, radio frequency identification ("RFID"), near field communications ("NEC"), biometrics, eye movement, facial recognition, head or body gestures. The emergency medical records will then be delivered to the medical provider and will contain one or more of the following: user profile data (photo, first name, middle name, last name, birthday, gender, blood type, race, primary language, secondary language, address, city, state, zip, height, weight, hair color, eye color, cell phone number, home phone number, work phone number, fax number, phone number, email address, insurance company name, group number, policy number, insurance phone number, organ donor (Yes or No), allow blood transfusions (yes or no), emergency contacts (first name, last name, address, city, state, zip code, cell phone number, work phone number, home phone number, email address, relationship), medications (name, dosage, how often), medical conditions (asthma, COPD, seizure disorder, dementia, Alzheimer's, hyperglycemia, hypoglycemia, diabetes type 1, diabetes type 2, high blood pressure, contact lenses, rheumatic fever, pacemaker, heart stent, fistula and so forth), allergies (name, description, notes/info), physician information (name, address, city, state, zip code, phone number, email address, specialty). The medical providers requesting the medical information is then documented with regard to his or her name, date and time of access, and GPS location when the information is requested.

A medical provider may include but is not limited to a hospital, urgent care center, physician's office, home health care, hospice, dentist's office, pharmacy, lab, ambulance service or any other provider of medical or medical related services. An employee of the medical provider may be referred to separately or fall within the definition of a service provider.

The above and other objects, features and advantages of the present invention should become even more readily apparent to those skilled in the art upon a reading of the following detailed description in conjunction with the drawings wherein there is shown and described illustrative embodiments of the invention.

BRIEF DESCRIPTION OF THE DRAWINGS

In the following detailed description, reference will be made to the attached drawings in which.

DESCRIPTION OF THE PREFERRED EMBODIMENTS

Figure 1:
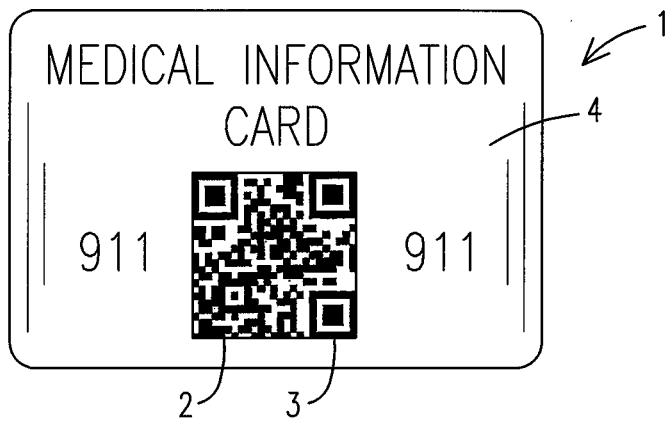
FIG. 1 is a front view of an identification card being used as a medical information device of the present invention.

With reference to FIG. 1, a front view of an identification card 4 being used as a medical information device 1 of the present invention is illustrated. The medical information device 1 allows an individual to store emergency medical information, such as blood type, allergies, medical conditions, present medications, age, doctor information and emergency contact information and to provide a means for retrieving that information to a medical provider. A medical provider may include but is not limited to a hospital, urgent care center, physician's office, home health care, hospice, dentist's office, pharmacy, lab, ambulance service or any other provider of medical or medical related services. An employee of the medical provider may be referred to separately or fall within the definition of a service provider. This is accomplished by using a machine-readable medium, such as a barcode 2, a Quick Response Code ("QR code") 3 or other matrix barcode, that is capable of storing text and/or URL information that may be opened by an electronic device or other imaging device, such as a smart phone. The barcode 2 may be printed directly on a medical information device 1, such as an identification card 4 (as illustrated here), a bracelet, a keychain, sleeve for an identification card and so forth.

Figure 2:
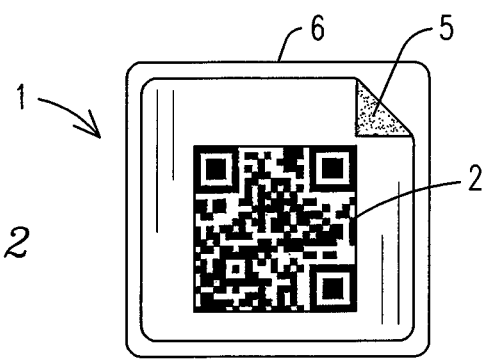
FIG. 2 is a front view of a barcode of the present invention printed on an adhesive-backed material.

With reference to FIG. 2, a front view of a barcode 2 of the present invention printed on an adhesive-backed material 5 is illustrated. The barcode 2 is a machine-readable medium that may have medical information directly stored therein and/or provide a URL for remote access of medical information stored in a central database. The barcode 2 illustrated here may be used by peeling off a backing 6 and adhering the adhesive backed material 5, such as paper, plastic, foil and so forth, to any object, such as an identification card, bracelet, keychain and so forth, sleeve for an identification card thereby making the object a medical information device 1.

Figure 3A:
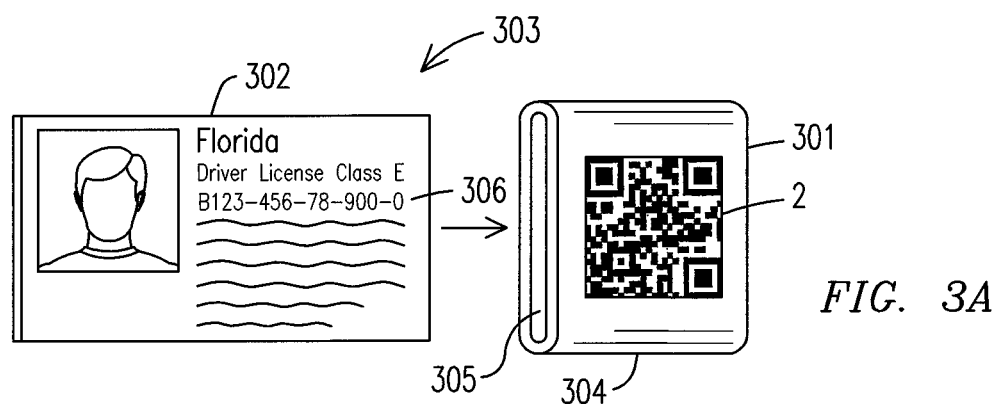
FIG. 3A is an exploded front perspective view of a sleeve for an identification card being used as a medical information device of the present invention.
Figure 3B:
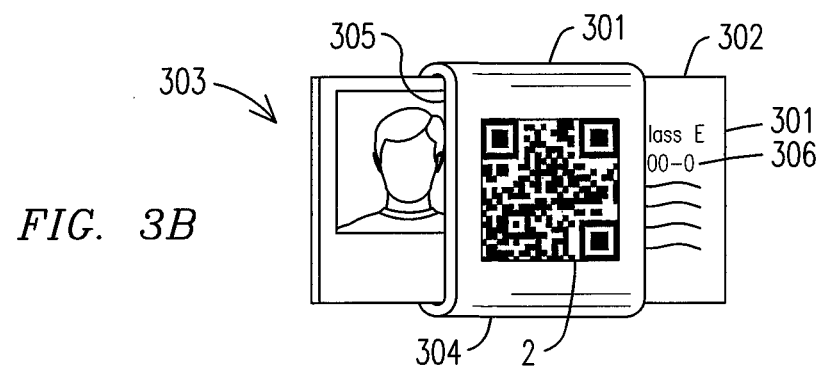
FIG. 3B is a front perspective view of a sleeve for an identification card being used as a medical information device of the present invention.

With reference to FIGS. 3A and 3B, an exploded front perspective view and a front perspective view, respectively, of a sleeve 301 for an identification card 302 being used as a medical information device 303 of the present invention are illustrated. The sleeve 301 comprises a perimeter wall 304 having at least one opening 305 to allow the identification card 302 to be inserted into the sleeve 301. A barcode 2 or other machine-readable medium electronic medium may be printed directly on the sleeve 301 or adhered to the sleeve 301 like a sticker. A new or pre-existing identification number 306, such as a driver's license number, insurance number and so forth, may be linked to an individual's account with the service provider so that it may be entered manually by a medical provider to access the individual's medical records.

Figure 4:
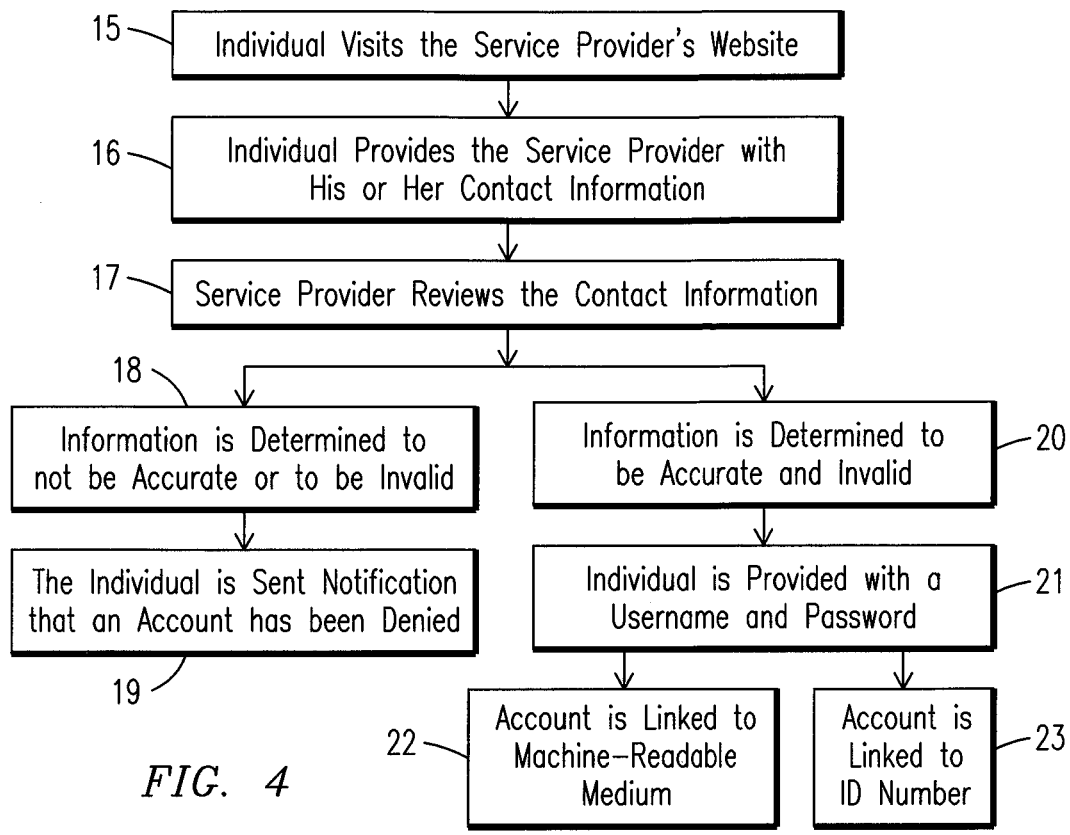
FIG. 4 is a flow chart showing an individual signing up for an account with a service provider that provides a medical information device to the individual.

With reference to FIG. 4, a flow chart showing an individual signing up for an account with a service provider that provides a medical information device to the individual is illustrated. First, the individual visits the service provider's website 15. Then, the individual provides the service provider with his or her contact information, which includes the individual's name, address, phone number, email address and so forth 16. The service provider then reviews the contact information to determine the accuracy of the information and the validity of the information 17. If the information is determined to not be accurate or to be invalid 18, then the individual is sent notification, preferably via email, that an account has been denied 19. If the information is determined to be accurate and valid 20, then the individual is sent an approval, preferably via email, that an account has been created and the individual is provided with a username and password 21. Next, the individual's account is liked to a machine-readable medium, such as a bar code, QR code, RFID, thumb drive, magnetic strip and so forth, 22 and/or to an identification number, such as a driver's license number, insurance number and so forth 23.

Figure 5:
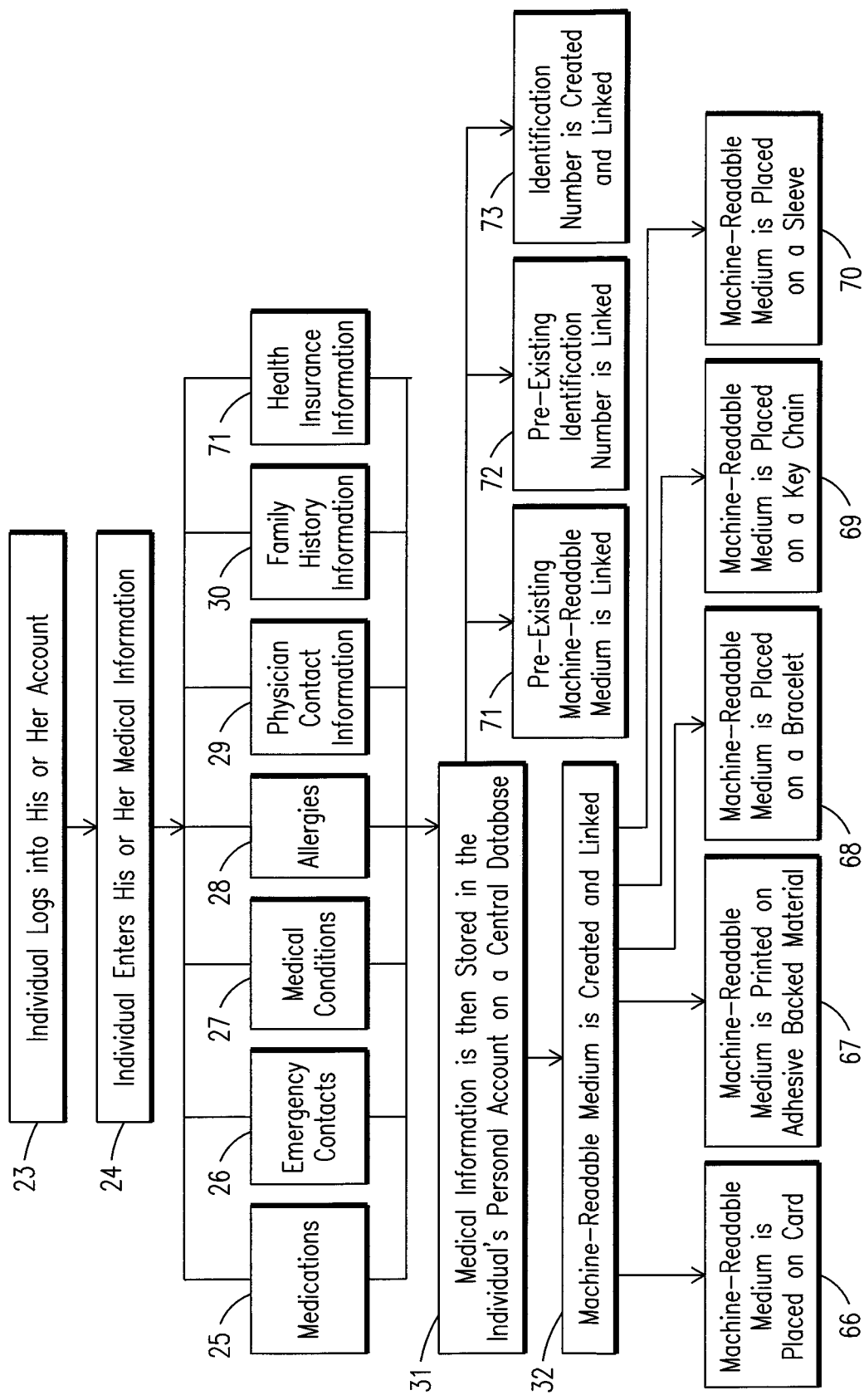
FIG. 5 is a flow chart showing the system and method of the present invention in which an individual enters medical information into an online account.

With reference to FIG. 5, a flow chart showing the system and method of the present invention in which an individual enters medical information into an online account is illustrated. First, the individual logs into his or her account using the username and password provided by the service provider 23. Then, the individual enters his or her medical information 24, which includes medications 25, emergency contacts 26, medical conditions 27, allergies 28, physician contact information 29, family history information 30, health insurance information 71 and so forth. The medical information is then stored in the individual's personal account in a central database 31. A bar code is then created that is personalized to the individual's account and has text medical information and/or a URL that directs a user to the individual's medical information remotely after the bar code is scanned 32. The bar code may be printed on an identification card 66, an adhesive backed material 67, a bracelet 68, a keychain 69, and/or a sleeve 70.

Figure 6:
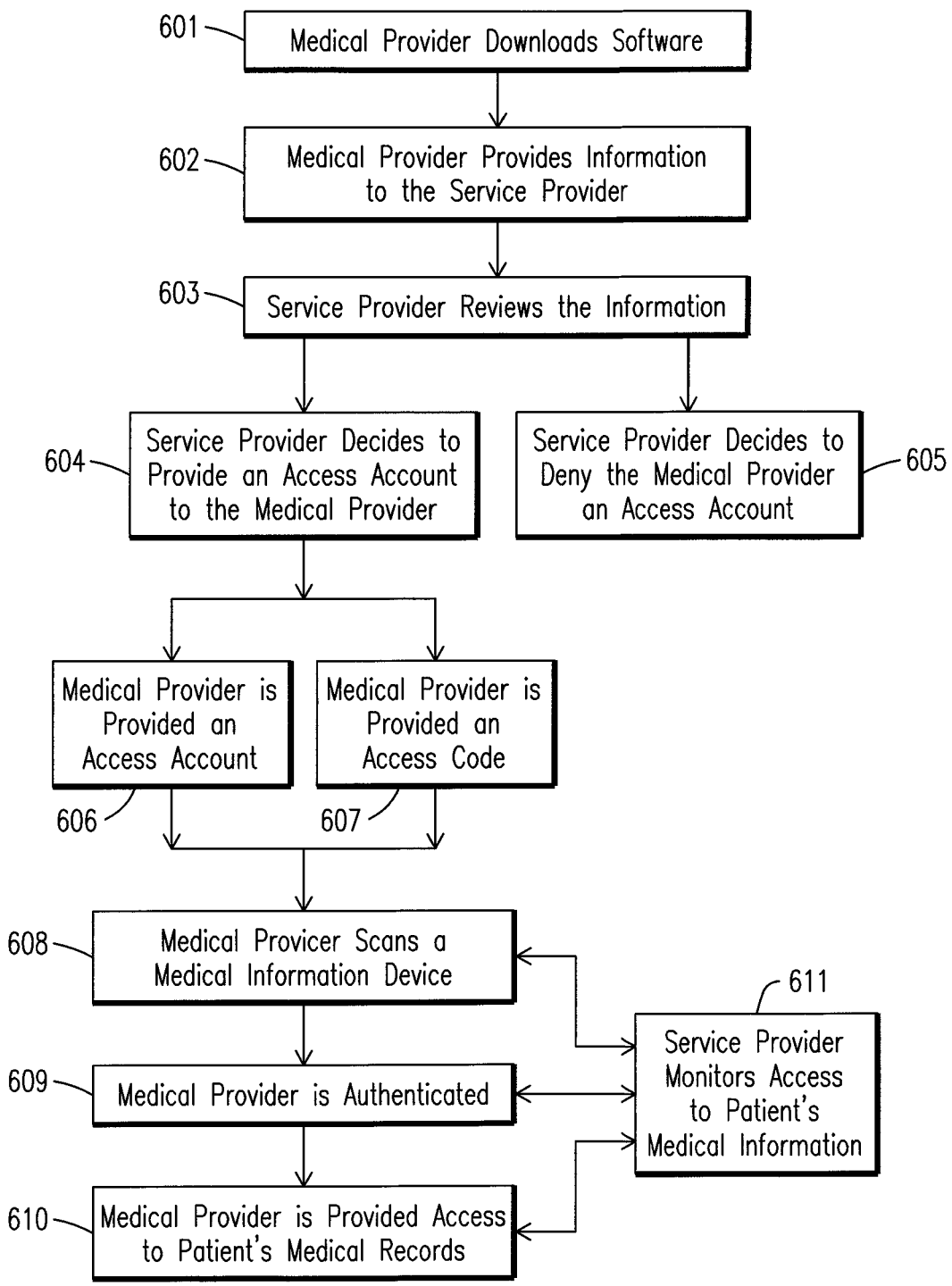
FIG. 6 is a flowchart showing the system and method of the present invention in which a medical provider is provided an account with the service provider to allow the medical provider to read medical information stored on a patient's medical information device and/or to access information remotely from the central database.

With reference to FIG. 6, a flowchart showing the system and method of the present invention in which a medical provider is provided an account with the service provider to allow the medical provider to read medical information stored on a patient's medical information device and/or to access information remotely from the central database is illustrated. This allows the medical provider to register or pre-register an individual, thereby allowing the medical provider to provide medical services more quickly and efficiently. First, the medical provider downloads a software application from the service provider 601. Said software application may be downloaded directly from the service provider or from any app store online over the Internet. Next, the medical provider registers his, her or its account by providing information, such as name, address, employer, position and so forth, to the service provider 602. The medical provider may also be required to provide government issued identification numbers confirming the medical provider's certifications. Then, the service provider reviews the information and determines if the information is correct and accurate 603. Next, the service provider decides to provide an access account to the medical provider 604 or denies the medical provider an access account 605. If the service provider decides to provide an access account to the medical provider 604, then the medical provider is provided an access account 606 and provided an access code 607 to allow the medical provider to read medical information stored on a patient's medical information device and/or to access information remotely from the central database through the service provider's website and/or through the downloaded mobile application software. When the medical provider scans an electronic storage means on a medical information device with an electronic device (such as a smart phone) using the downloaded software 608, the medical provider is required to enter the access code or to be authenticated by other means, such as biometric scans, 609 prior to obtaining access to any medical information stored directly on the medical information device and/or accessing information remotely from the central database 610. The service provider is then able to ensure that medical information is kept private. The service provider is then able to monitor who is accessing a patient's medical information and when and where the medical information is being accessed 611.

Figure 7:
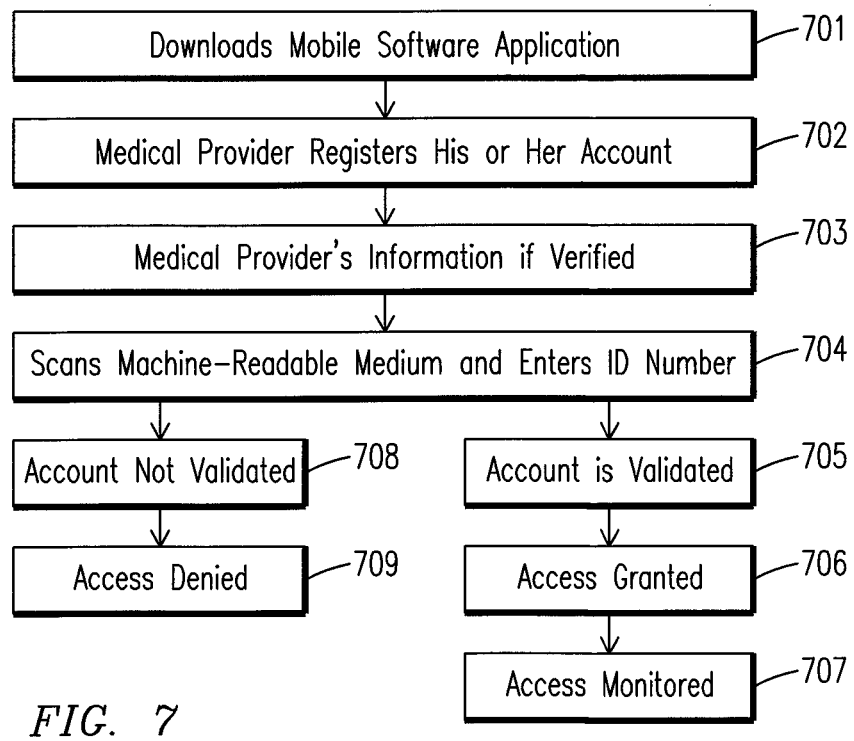
FIG. 7 is a flowchart showing the system and method of the present invention in which a medical provider downloads a mobile software application from the service provider and the authentication of the medical provider.

With reference to FIG. 7, a flowchart showing the system and method of the present invention in which a medical provider downloads a mobile software application from the service provider and the authentication of the medical provider is illustrated. First, a medical provider downloads a mobile software application to their electronic device from an APP store or directly from the service provider 701. Then, the medical provider registers his or her account using a state issued license number or other relevant information 702. Next, the information is verified so the medical provider may use the software and/or the service provider's website to access an individual's electronic emergency medical records 703. Then, the medical provider scans a bar code or other machine-readable medium or manually inputs an identification number of the individual receiving treatment 704. Next, the medical provider's registration with the service provider is validated to ensure it has not expired or become invalid 705. If valid, then the individual's medical records are displayed 706, and the medical provider's access is logged 707 with regard to time and date the medical provider accessed the record and the geo-location including the longitude/latitude of where the record was accessed. If not valid, an indicator is provided to the medical provider that his, her or its registration is not valid 708 and access is denied.

Figure 8:
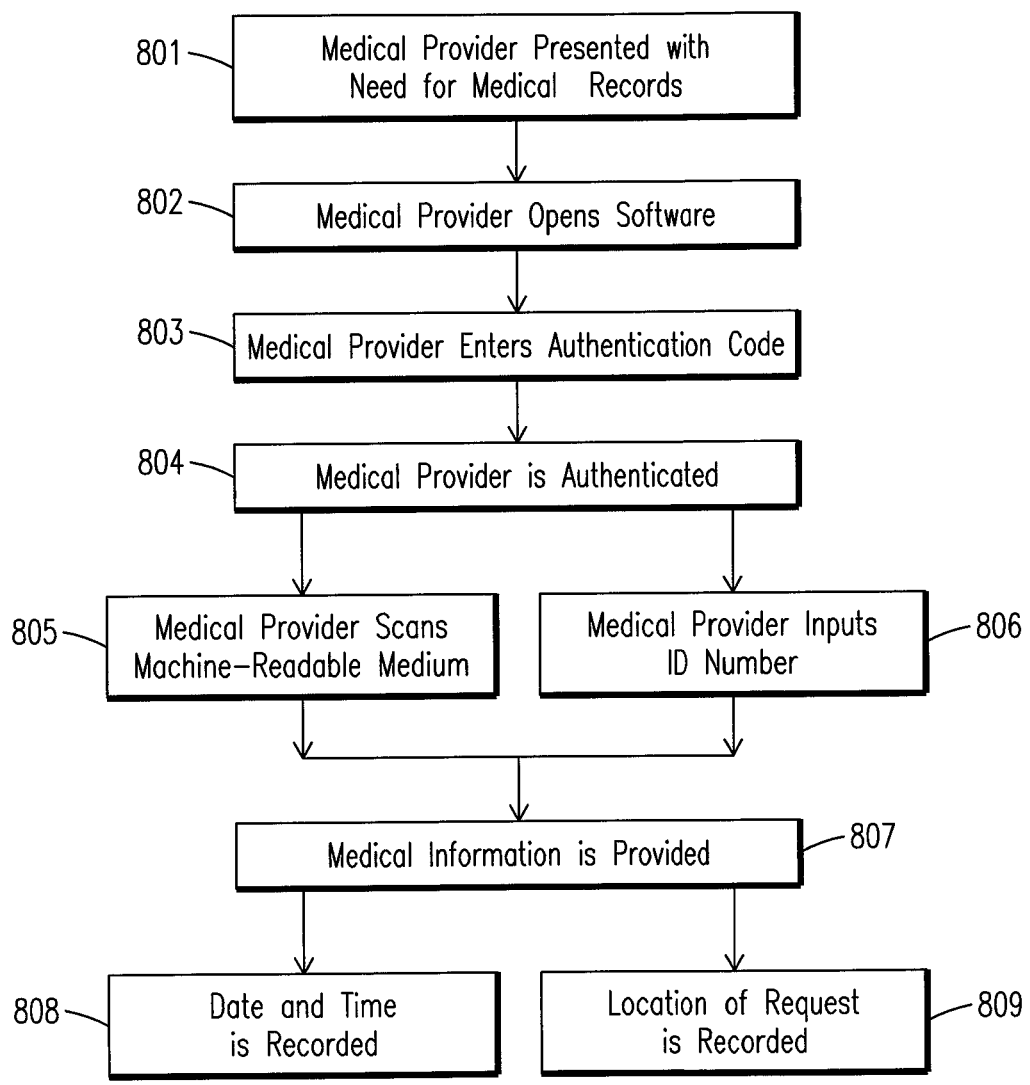
FIG. 8 is a flowchart showing the system and method of the present invention in which a medical provider retrieves medical information from a patient's medical information device.

With reference to FIG. 8, a flowchart showing the system and method of the present invention in which a medical provider retrieves medical information from a patient's medical information device is illustrated. First, a medical provider responds to and/or is presented with a medical emergency or other need to access an individual's medical records 801. Then, the medical provider locates the machine-readable medium 802. Next, the medical provider opens the service provider's software on his or her electronic device 803. Then, the medical provider enters his or her authentication code or other identifying means 804. Next, the medical provider scans the machine-readable medium using the electronic device 805 or enters the individual's identification number, such as a driver's license number 806. Then, the medical information is provided to the medical provider 807. Next, the time and date of the request is recorded 808, and the location of the request is recorded 809.

It is to be understood that while a preferred embodiment of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

Having thus described my invention, I claim:

1. A method for storing medical information of an individual with a service provider and providing access to that medical information to medical providers comprising the steps of:
   a. an individual providing the service provider with his or her contact information;
   b. the service provider reviewing the contact information and rendering a decision on whether to allow the individual to have an account;
   c. an individual creating an account with a service provider over the internet;
   d. the individual's medical information being provided to the service provider to be saved in a central database;
   e. the service provider authenticating a medical provider;
   f. the medical provider being provided an account with the service provider; and
   g. the service provider providing medical provider with remote access to the individual's medical information.

2. The method of claim 1 further comprising steps of:
   the service provider deciding to allow the individual to have an account; and
   the service provider creating an account and providing the individual with a username and password.

3. The method of claim 1 further comprising a step of:
the service provider linking the individual's account to a machine-readable medium.

4. The method of claim 1 further comprising a step of:
the service provider linking the individual's account to an identification number.

5. The method of claim 1 further comprising a step of:
the medical provider downloading software from the service provider onto an electronic device.

6. The method of claim 3 further comprising a step of:
the medical provider scanning the machine-readable medium using an electronic device and obtaining the individual's medical information from the service provider.

7. The method of claim 4 further comprising a step of:
the medical provider entering the identification number into an electronic device and obtaining the individual's medical information from the service provider.

8. The method of claim 6 further comprising a step of:
the date and time the medical provider scanned the machine-readable medium being recorded by the service responder.

9. The method of claim 7 further comprising a step of:
the date and time the medical provider uses the individual's identification number to obtain the individual's medical records being recorded by the service responder.

10. The method of claim 6 further comprising a step of:
the location of the medical provider when the medical provider scanned the machine-readable medium being recorded by the service responder.

11. The method of claim 7 further comprising a step of:
the location of the medical provider when the medical provider used the individual's identification number to obtain the individual's medical records being recorded by the service responder.

12. A system for storing medical information of an individual with a service provider and providing access to that medical information to medical providers comprising:
an individual providing the service provider with his or her contact information;
the service provider reviewing the contact information and rendering a decision on whether to allow the individual to have an account;
an individual creating an account with a service provider over the internet;
the individual's medical information being provided to the service provider to be saved in a central database;
the service provider authenticating a medical provider;
the medical provider being provided an account with the service provider; and
the service provider providing medical provider with remote access to the individual's medical information.

13. The system of claim 12 further comprising:
the service provider deciding to allow the individual to have an account; and
the service provider creating an account and providing the individual with a username and password.

* * * * *